US00PP22663P3

(12) United States Plant Patent
Bartels

(10) Patent No.: US PP22,663 P3
(45) Date of Patent: Apr. 17, 2012

(54) ***PHLOX* PLANT NAMED 'BARSIXTYTHREE'**

(50) Latin Name: *Phlox paniculata*
Varietal Denomination: Barsixtythree

(75) Inventor: Gosen B. H. Bartels, Aalsmeer (NL)

(73) Assignee: Bartels Breeding B.V., Aalsmeer (NL)

( * ) Notice: Subject to any disclaimer, the term of this patent is extended or adjusted under 35 U.S.C. 154(b) by 32 days.

(21) Appl. No.: 12/802,686

(22) Filed: Jun. 11, 2010

(65) Prior Publication Data

US 2011/0307985 P1 Dec. 15, 2011

(51) Int. Cl.
*A01H 5/00* (2006.01)

(52) U.S. Cl. ..... Plt./320

(58) Field of Classification Search ..... Plt./320
See application file for complete search history.

(56) References Cited

U.S. PATENT DOCUMENTS

PP20,569 P2 * 12/2009 Tonies ..... Plt./320

* cited by examiner

*Primary Examiner* — June Hwu

(74) *Attorney, Agent, or Firm* — Jondle & Associates, P.C.

(57) ABSTRACT

A new *Phlox paniculata* plant particularly distinguished by a vigorous growth habit and purple inflorescences is disclosed.

2 Drawing Sheets

Genus and species: *Phlox paniculata.*
Variety denomination: 'Barsixtythree'.

BACKGROUND OF THE NEW PLANT

The present invention comprises a new and distinct variety botanically known as *Phlox paniculata*, and hereinafter referred to by the variety name 'Barsixtythree'. The new variety originated from a crossing made in 2003 in Aalsmeer, The Netherlands. The female parent was the proprietary *Phlox paniculata* plant '00-48-02' (unpatented), while the male parent was the proprietary *Phlox paniculata* plant '00-77-01' (unpatented).

'Barsixtythree' was first propagated by vegetative cuttings in 2003 in Aalsmeer, The Netherlands and has been subsequently asexually propagated by vegetative cuttings in Aalsmeer, The Netherlands since 2003. The present invention has been found to retain its distinctive characteristics through successive asexual propagations via vegetative cuttings.

Plant Breeder's Rights for this variety were applied for in May 2010 for Europe. 'Barsixtythree' has not been made publicly available or sold more than one year prior to the filing date of this application.

SUMMARY OF THE INVENTION

The following are the most outstanding and distinguishing characteristics of this new variety when grown under normal horticultural practices in Aalsmeer, The Netherlands.

1. A vigorous growth habit; and
2. Purple inflorescences.

DESCRIPTION OF THE PHOTOGRAPHS

This *Phlox paniculata* plant is illustrated by the accompanying photographs which show the overall plant habit including blooms, buds, and foliage of the plant. The colors shown are as true as can be reasonably obtained by conventional photographic procedures.

Figure 1:
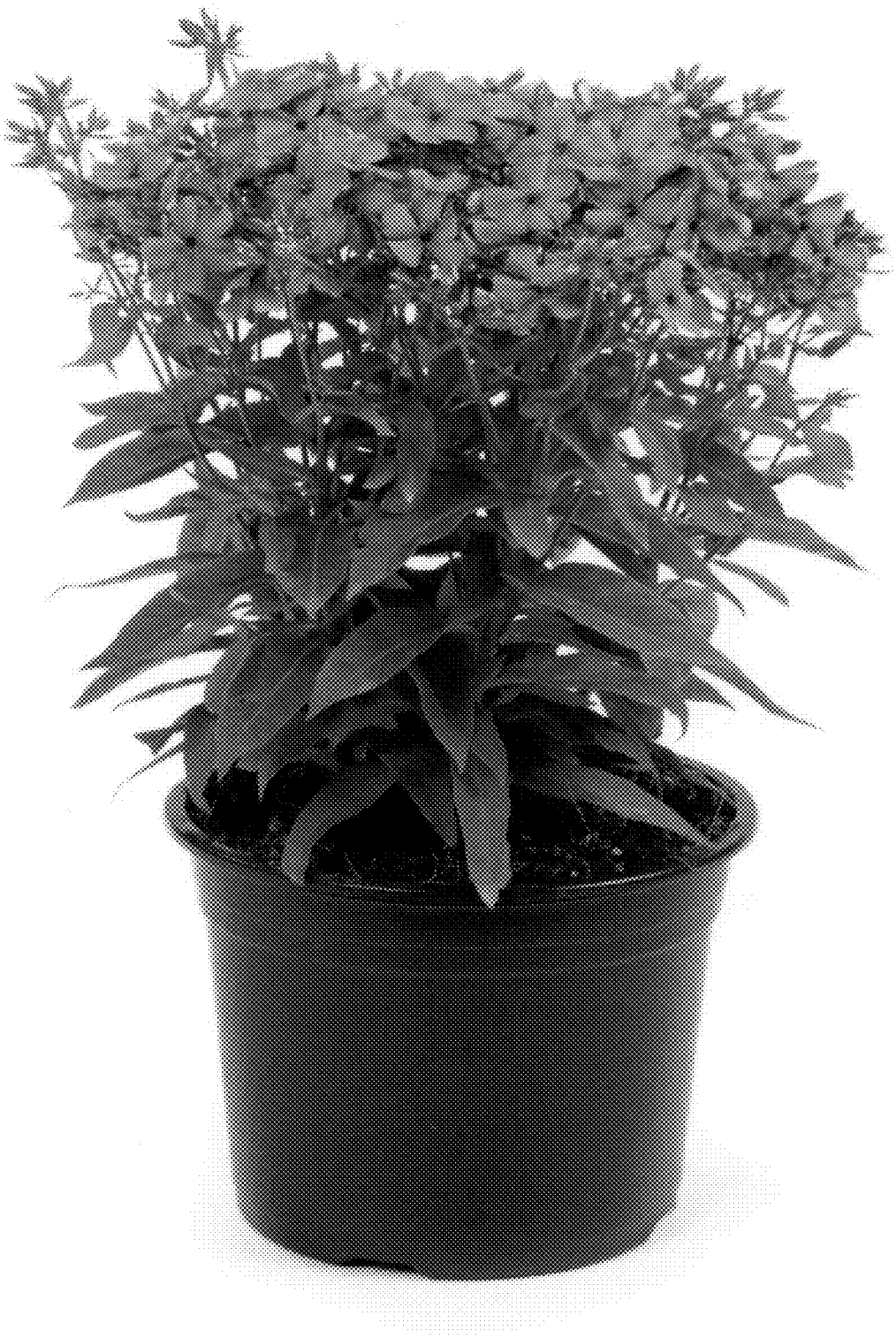
Figure 2:
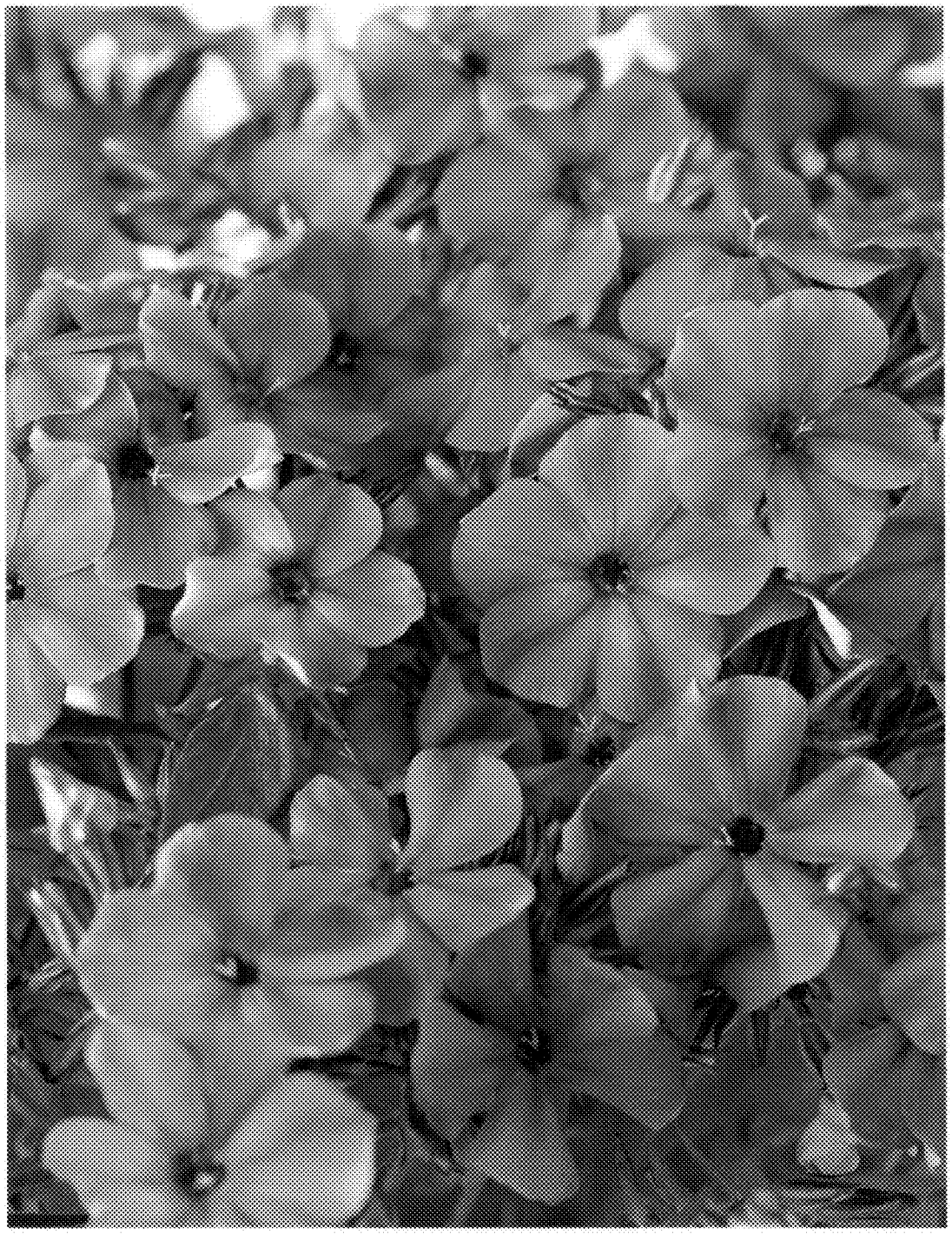

FIG. 1 shows the overall plant habit.
FIG. 2 shows a close-up of an inflorescence.

DESCRIPTION OF THE NEW VARIETY

The following detailed description sets forth the distinctive characteristics of 'Barsixtythree'. The data which defines these characteristics were collected from asexual reproductions carried out in Aalsmeer, The Netherlands in spring/early summer 2010. Color readings were taken under natural light outdoors. Color references are primarily to The R.H.S. Colour Chart of The Royal Horticultural Society of London (R.H.S.) (1986).

DETAILED BOTANICAL DESCRIPTION

Classification:
- *Family.*—Polemoniaceae.
- *Botanical name.—Phlox paniculata.*
- *Common name.*—Phlox.
- *Denomination.*—'Barsixtythree'.

Plant:
- *Growth habit.*—Vigorous.
- *Form.*—Narrow, bushy.
- *Habit.*—Upright.
- *Height (measured from the top of the soil).*—25.0 cm to 30.0 cm.
- *Diameter or area of spread.*—25.0 cm.
- *Propagation.*—Via vegetative cuttings.
- *Time to produce a finished flowering plant.*—4 months.
- *Lastingness of inflorescence on the plant.*—4 weeks.
- *Outdoor plant performance.*—Very good.
- *Time to initiate and develop roots.*—2 weeks.
- *Time to produce rooted cutting or liner (young plant)* .—5 weeks.
- *Root description.*—White fibrous.

Branches:
- *Number of branches per plant.*—5.
- *Length of lateral branches.*—25.0 cm to 30.0 cm.

*Diameter of a cluster of lateral branches.*—15.0 cm.
*Texture*.—Smooth with rough, corky surface texture at bottom.

Stems:
*Shape in cross-section*.—Circular.
*Aspect*.—Smooth.
*Color*.—RHS 143C.
*Diameter*.—5.0 mm to 8.0 mm.
*Stem length*.—40.0 cm.
*Internode length*.—3.0 cm to 4.0 cm.
*Anthocyanin*.—Present; RHS 187A.
*Pubescence*.—Present.

Leaves:
*Arrangement*.—Alternate.
*Quantity of leaves* (*per lateral branch*).—26 to 30.
*Apex*.—Acute.
*Base*.—Rounded.
*Color* (*mature and immature leaves*).—Upper surface: RHS 137A. Lower surface: RHS 137B.
*Margin*.—Smooth.
*Length*.—8.0 cm.
*Width*.—3.0 cm.
*Shape*.—Lanceolate.
*Texture* (*both surfaces*).—Smooth.
*Pubescence*.—Upper surface: Few. Lower surface: Absent.
*Venation type*.—Featherlike.
*Venation color*.—RHS 144B.
*Petiole*.—Color: RHS 144B. Length: 4.0 mm. Diameter: 3.0 mm. Texture: Smooth.

Flower buds:
*Color*.—RHS 86C.
*Shape*.—Oblong.
*Length*.—18.0 mm.
*Diameter*.—4.0 mm.

Inflorescence:
*Blooming habit*.—Flat-topped shaped panicle.
*Blooming season* (*indoor*).—May to September.
*Blooming season* (*outdoor*).—July to September.
*Inflorescence type*.—Terminal panicle.
*Arrangement*.—Terminal and lateral.
*Number of flowers per inflorescence*.—30 to 50.
*Quantity of flowers and buds per plant*.—Approximately 120.
*Height*.—15.0 cm.
*Width*.—15.0 cm.
*Shape*.—Flat-topped.
*Fragrance*.—Present.
*Peduncle*.—Color: RHS 143A. Length: 15.0 cm. Diameter: 0.6 cm. Texture: Smooth. Pubescence: Few.
*Pedicel*.—Color: RHS 143A. Length: 1.0 cm. Diameter: 0.2 cm. Texture: Smooth.

Flowers:
*Flower type*.—Actinomorphic.
*Height* (*flower depth*).—2.0 cm.
*Diameter*.—2.0 cm.
*Flower tube length*.—1.5 cm.
*Throat diameter*.—4.0 mm.
*Color of flower throat*.—RHS 71B.
*Texture* (*both surfaces*).—Smooth.
*Corolla*.—Shape: Circular. Color: Inside: RHS 80A. Outside: RHS 84C. Length: 2.0 cm. Diameter: 2.0 cm.
*Petals*.—Arrangement: Single whorl. Lobe shape: Rotundate-ovate. Number (per flower): 5. Length (from the throat): 1.0 cm. Width: 7.0 mm. Apex: Obcordate. Base: Fused. Margin: Smooth. Color (when opening): Upper surface: RHS 80A. Lower surface: RHS 84C. Color (fully opened): Upper surface: RHS 80A. Lower surface: RHS 84C fading to RHS 78D. Petal pubescence (both surfaces): Absent.
*Calyx*.—Shape: Funnel. Length: 12.0 mm. Diameter: 3.0 mm.
*Sepals*.—Arrangement: Single whorl. Number: 5. Shape: Narrow triangular. Apex: Pointed. Base: Fused. Margin: Smooth. Length: 10.0 mm. Width: 1.0 mm to 2.0 mm. Texture (both surfaces): Smooth. Color (mature; both surfaces): RHS 147A. Color (immature; both surfaces): RHS 143C.

Reproductive organs:
*Quantity of stamens* (*per flower*).—5.
*Anther*.—Shape: Linear. Length: 0.2 cm. Color: RHS 8C.
*Filament color*.—RHS 155A.
*Pollen amount*.—Few.
*Pollen color*.—RHS 155A.
*Pistil*.—Quantity (per flower): 1. Length: 16.0 mm.
*Style*.—Length: 20.0 mm. Color: RHS 144B.
*Stigma*.—Shape: 3 lobes. Color: RHS 144B.
*Ovary color*.—RHS 143A.

Seed: None observed.

Disease and insect resistance: Slightly susceptible to powdery mildew.

COMPARISON WITH COMMERCIAL VARIETY

'Barsixtythree' differs from the commercial variety 'Barfourteen' (U.S. Plant Pat. No. 12,605) in that 'Barsixtythree' has a flat flowering canopy, smaller-sized flowers (1.5 cm), and an earlier flowering time, while 'Barfourteen' has a raceme-like flowering canopy, larger-sized flowers (2.0 cm to 3.0 cm), and the flowering time is two to three weeks later than 'Barsixtythree'.

I claim:

1. A new and distinct variety of *Phlox paniculata* plant as described and shown herein.

* * * * *